(12) United States Patent
Li et al.

(10) Patent No.: US 10,004,275 B2
(45) Date of Patent: Jun. 26, 2018

(54) ATOMIZER AND ELECTRONIC CIGARETTE HAVING SAME

(71) Applicant: Shenzhen First Union Technology Co., Ltd., Shenzhen, Guangdong Providence (CN)

(72) Inventors: Yonghai Li, Shenzhen (CN); Zhongli Xu, Shenzhen (CN); Changzheng Dai, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 0 days. days.

(21) Appl. No.: 15/480,362

(22) Filed: Apr. 5, 2017

(65) Prior Publication Data
US 2017/0208869 A1   Jul. 27, 2017

(30) Foreign Application Priority Data

Apr. 14, 2016  (CN) ...................... 2016 2 0309733 A

(51) Int. Cl.
*A24F 47/00*    (2006.01)
*F16L 55/115*   (2006.01)

(52) U.S. Cl.
CPC ........... *A24F 47/008* (2013.01); *F16L 55/115* (2013.01)

(58) Field of Classification Search
CPC .................................................... F16L 55/115
USPC ........................................................ 131/329
See application file for complete search history.

(56) References Cited

U.S. PATENT DOCUMENTS

| | | | | |
|---|---|---|---|---|
| 2013/0192623 | A1* | 8/2013 | Tucker ............. | H01C 17/00 131/329 |
| 2015/0034102 | A1* | 2/2015 | Faramarzian ........ | A24F 47/008 131/328 |
| 2015/0034103 | A1* | 2/2015 | Hon ................. | A24F 47/008 131/328 |
| 2015/0245660 | A1* | 9/2015 | Lord ................ | A24F 47/008 131/328 |
| 2016/0157522 | A1* | 6/2016 | Zhu ................. | A24F 47/008 131/329 |
| 2016/0235121 | A1* | 8/2016 | Rogan ............... | A24D 3/041 |

(Continued)

FOREIGN PATENT DOCUMENTS

WO    WO 2016029567 A1 *   3/2016   ............. A24F 47/00

*Primary Examiner* — Tulsidas C Patel
*Assistant Examiner* — Travis Chambers
(74) *Attorney, Agent, or Firm* — Cheng-Ju Chiang

(57) ABSTRACT

The present disclosure relates to an atomizer for an electronic cigarette. The atomizer includes a housing, a sealing cover, a mouthpiece, an atomizing device, and an air pipe. The housing has a first end and a second end. The housing defines a liquid chamber configured for containing tobacco liquid. The atomizing device is configured for atomizing the tobacco liquid to form aerosol. The first end defines a liquid filling opening in communication with the liquid chamber. When the sealing cover is connected with the first end, the sealing cover seals the liquid filling opening. The sealing cover defines an air inlet. The air pipe and the liquid chamber cooperatively define an annular air passage in communication with the air inlet, so that external air can enter the air inlet and reach the atomizing device through the air passage, and then together with the aerosol can be expelled via the mouthpiece.

8 Claims, 7 Drawing Sheets

(56) References Cited

U.S. PATENT DOCUMENTS

2017/0086506 A1\* 3/2017 Rado .................... A24F 47/008
2017/0208864 A1\* 7/2017 Anderson, Jr. ....... A24F 47/008

\* cited by examiner

ATOMIZER AND ELECTRONIC CIGARETTE HAVING SAME

TECHNICAL FIELD

The present invention relates to electronic cigarettes, and particularly to an atomizer and an electronic cigarette using same.

BACKGROUND ART

A typical atomizer includes a housing with a first end and an opposite second end. A mouthpiece is provided at the first end, and an air inlet is defined in the second end. During transportation or in use, the tobacco liquid may leak from the air inlet, rendering unsatisfactory.

What are needed, therefore, are an atomizer and an electronic cigarette using same, which can overcome the above shortcomings.

SUMMARY

The present disclosure relates to an atomizer for an electronic cigarette. The atomizer includes a housing, a sealing cover, a mouthpiece, an atomizing device, and an air pipe. The housing has a first end and a second end. The housing defines a liquid chamber configured for containing tobacco liquid. The atomizing device is configured for atomizing the tobacco liquid to form aerosol. The first end defines a liquid filling opening in communication with the liquid chamber. When the sealing cover is connected with the first end, the sealing cover seals the liquid filling opening. The sealing cover defines an air inlet. The air pipe and the liquid chamber cooperatively define an annular air passage in communication with the air inlet, so that external air can enter the air inlet and reach the atomizing device through the air passage, and then together with the aerosol can be expelled via the mouthpiece.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
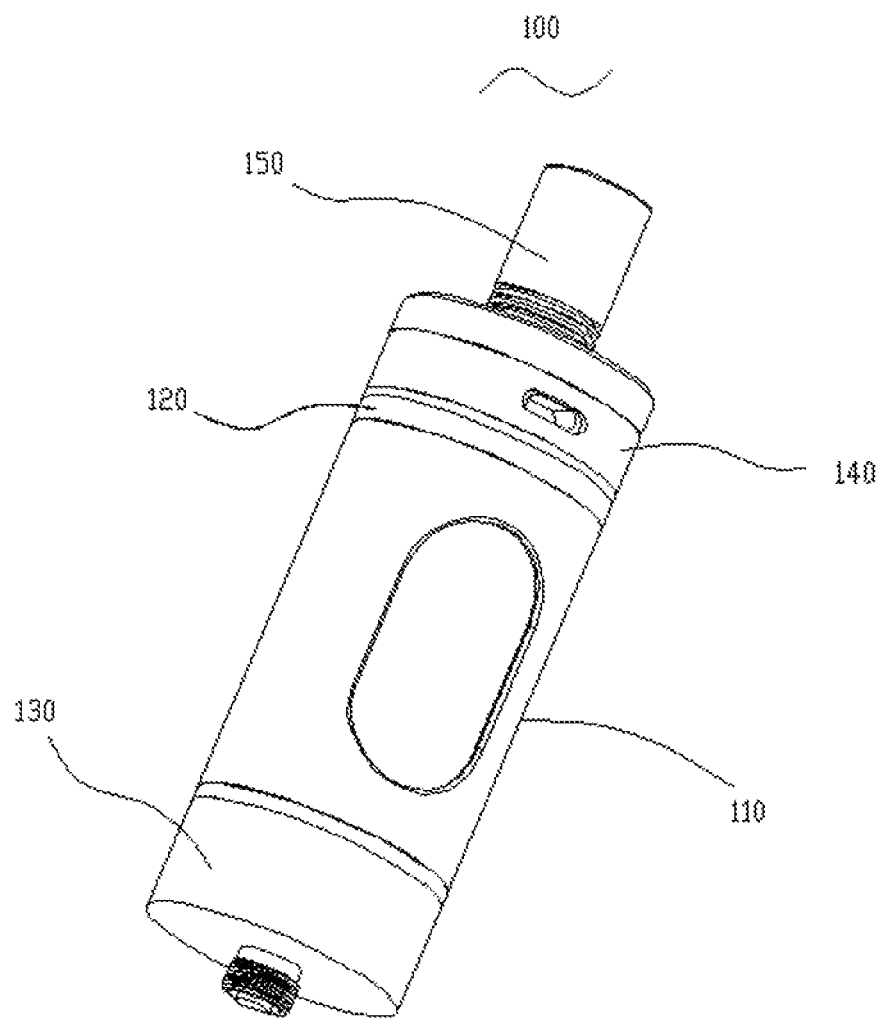
FIG. 1 is a perspective view of an atomizer according to a first embodiment, including a sealing cover, a liquid filling opening, an air pipe and an air adjusting ring.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 2:
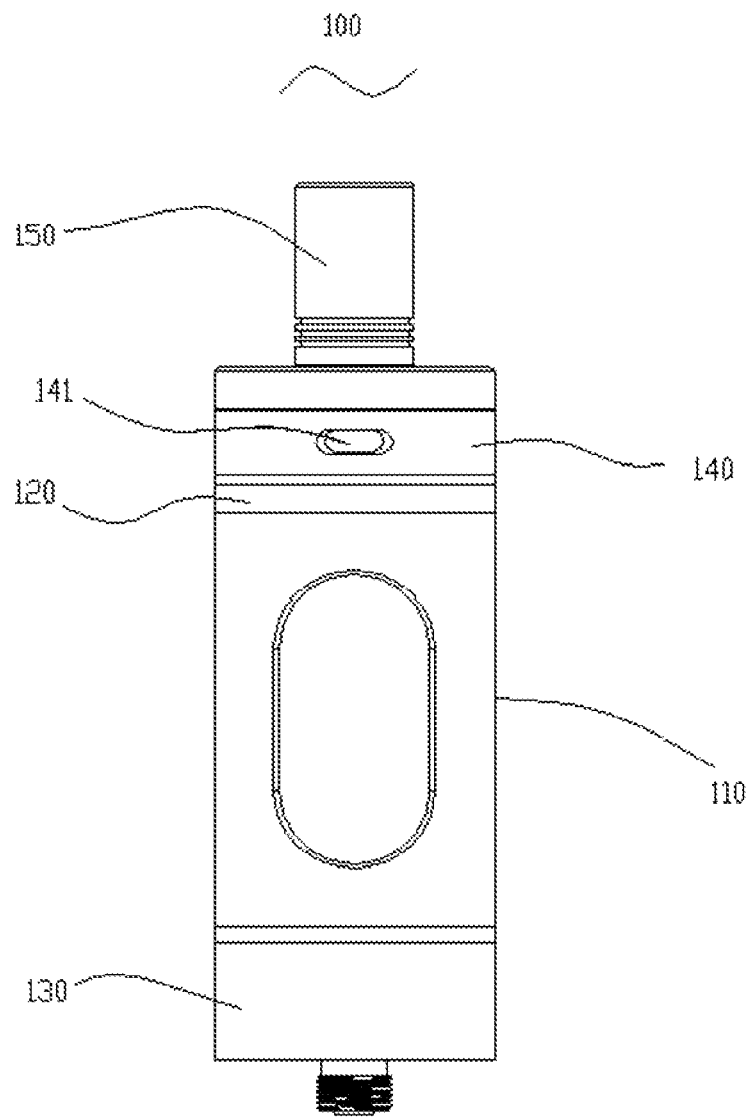
FIG. 2 is a side view of the atomizer of FIG. 1.
Figure 3:
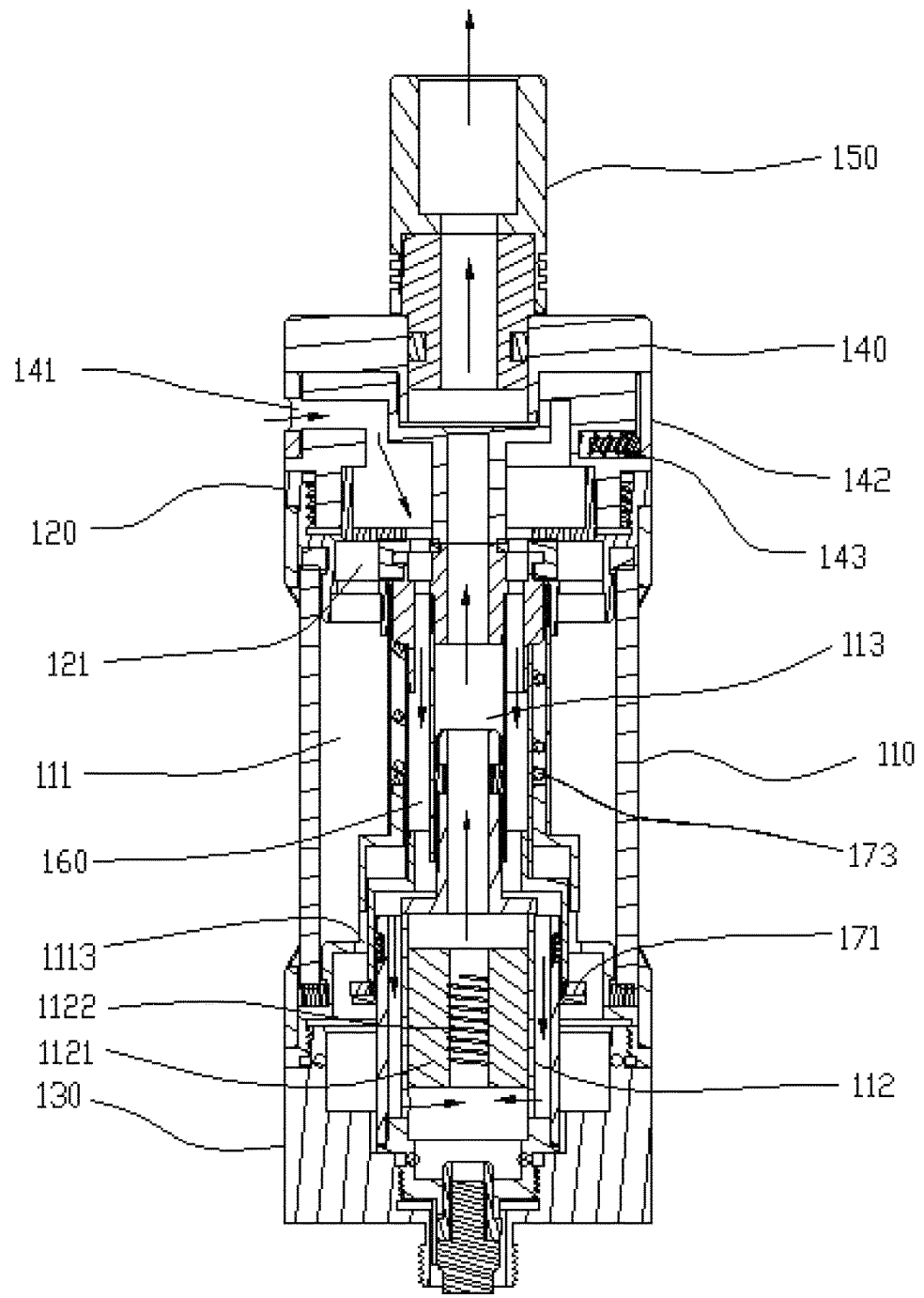
FIG. 3 is a cross-sectional view of the atomizer.

Referring to FIGS. 1-2, an atomizer 100 is shown. The atomizer 100 is configured (i.e., structured and arranged) for coupling with a power supply 200 to form an electronic cigarette (referring to FIG. 7). The atomizer 100 includes a housing 110, a sealing cover 140, and a mouthpiece 150. The housing 110 includes a first end 120 and an opposite second end 130. The sealing cover 140 is detachably connected with the first end 120. The mouthpiece 150 is connected with the sealing cover 140. The second end 130 is configured for connecting with the power supply 200. Referring to FIG. 3, a liquid chamber 111, an atomizing device 112, and an air pipe 113 are provided in the housing 110. The liquid chamber 111 is configured for containing tobacco liquid. The atomizing device 112 is configured for atomizing the tobacco liquid to form aerosol. The air pipe 113 allows the aerosol to pass through. The first end 120 defines a liquid filling opening 121 in communication with the liquid chamber 111. After the sealing cover 140 is connected to the first end 120, the sealing cover 140 seals the liquid filling opening 121, thus avoiding liquid leakage. The sealing cover 140 further defines an air inlet 141. An annular air passage 160 is defined between the air pipe 113 and the liquid chamber 111. The air passage 160 is in communication with the air inlet 141. External air goes in via the air inlet 141, passes through the air passage 160 to reach the atomizing device 112, brings the aerosol to pass through the air pipe 113, and is then expelled via the mouthpiece 150.

Figure 4:
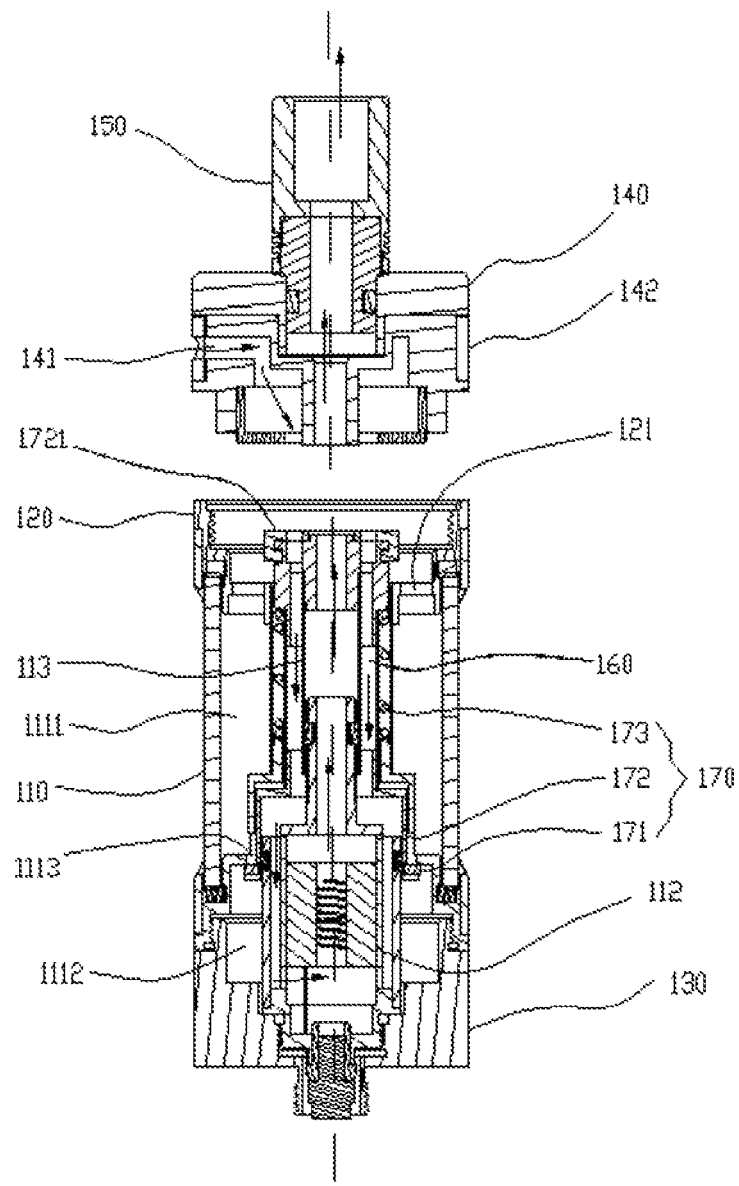
FIG. 4 is a cross-sectional view of the atomizer when the sealing cover is detached.

Referring to FIGS. 3-4, the liquid chamber 111 includes a storing chamber 1111 and a buffer chamber 1112, and the liquid filling opening 121 is in communication with the storing chamber 1111. The buffer chamber 1112 is more adjacent to the second end than the storing chamber 1111.

The air pipe 113 is arranged in the liquid chamber 1111, and the atomizing device 112 is arranged in the buffer chamber 1112, and is in communication with the air pipe 113. The atomizing device 112 absorbs tobacco liquid in the buffer chamber 1112. A liquid passage 1113 is defined between the storing chamber 1111 and the buffer chamber 1112. A valve 170 is provided in the liquid passage 1113 and configured for opening or closing the liquid passage 1113.

The atomizing device 112 includes a liquid conducting element 1121 and a heating element 1122 in contact with the liquid conducting element 1121. The liquid conducting element 1121 is configured for absorbing the tobacco liquid in the buffer chamber 1112. The liquid conducting element 1121 may be made of cotton, glass fiber, or ceramic. In the present embodiment, the heating element 1122 is oriented along an axial direction of the air pipe 113.

Figure 5:
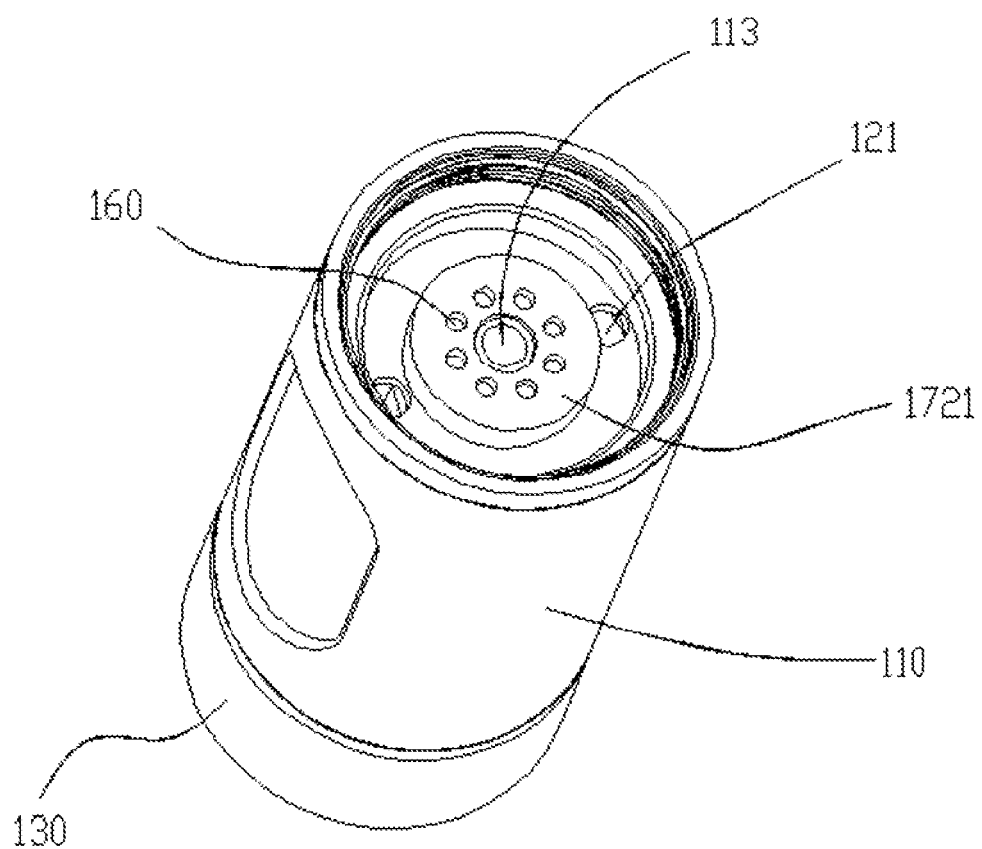
FIG. 5 is a perspective view of the atomizer when the sealing cover is detached, exposing the liquid filling opening and the air pipe.

Referring to FIGS. 4-5, the valve 170 includes a sealing element 171, a movable element 172, and a spring 173. The sealing element 171 is configured for sealing the liquid passage 1113. The sealing element 171 is arranged on the movable element 172. The spring 173 abuts against the movable element 172. The movable element 173 is nested in the air passage 160, and extends to the first end 120. When the sealing cover 140 is connected with the first end 120, the sealing cover 140 abuts against an extension end 1721 of the movable element 172, and the movable element 172 drives the sealing element 171 to move along an axial direction of the housing 110 and compresses the spring 173. In this way, the liquid passage 1113 is opened, and the tobacco liquid in the liquid chamber 1111 flows into the buffer chamber 1112 via the liquid passage 1113. When the sealing cover 140 is detached from the first end 120, the movable element 172 drives the sealing element 171 to seal the liquid passage 1113 upon a restoring force of the spring 173. The sealing element 171 may be made of rubber or silicone.

When filling in tobacco liquid, the sealing cover 140 is first detached, the movable element 172 drives the sealing element 171 to seal the liquid passage 1113 upon a restoring force of the spring 173, so that tobacco liquid can only flow into the liquid chamber 1111. After finishing the filling of tobacco liquid, the sealing cover 140 is assembled to abut against the extension end 1721 of the movable element 172, so that the movable element 172 drives the sealing element 171 to move along an axial direction thereof to compress the spring 173. In this way, the liquid passage 1113 is opened, the tobacco liquid in the liquid chamber 1111 flows into the buffer chamber 1112 via the liquid passage 1113.

Figure 6:
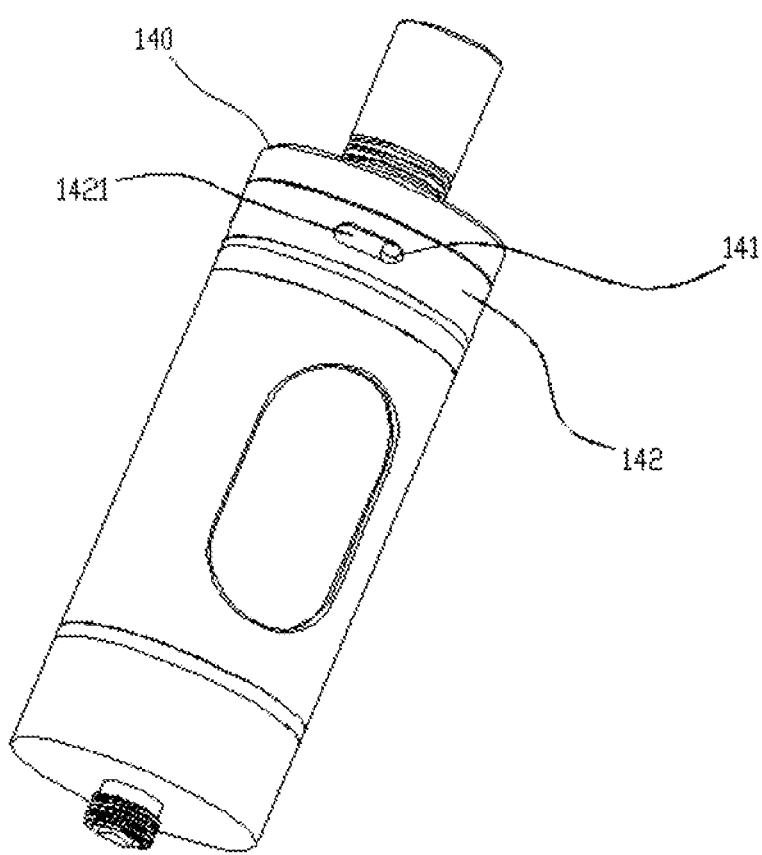
FIG. 6 is a perspective view of the atomizer when the air adjusting ring is rotated a certain angle.

Referring to FIGS. 2 and 6, in the present embodiment, an air adjusting ring 142 is provided and nests the sealing cover 140 adjacent to the air inlet 141. The air adjusting ring 142 defines a through hole 1421, and is rotatable relative to the sealing cover 140, such that an overlapping area between the through hole 1421 and the air inlet 141 can be changed. Accordingly, an amount of incoming air can be changed.

Referring to FIG. 3, an abutting device 143 is further provided abutting against the air adjusting ring 142 on the sealing cover 140. The abutting device 143 is configured for providing a force on the air adjusting ring 142 along a radial direction of the air adjusting ring 142, thus preventing the air adjusting ring 142 from rotating relative to the sealing cover 140 casually. When manually rotating the air adjusting ring 142 relative to the sealing cover 140, the force exerting by the abutting device 143 can be overcome.

In the present embodiment, the air inlet 141 is defined in the sealing cover 140, the sealing cover 140 is arranged at the first end 120, and the atomizing device 112 is arranged at the second end 130. The annular air passage 160 connects the atomizing device 112 and the air inlet 141, and accordingly a distance between the air inlet 141 and the atomizing device 112 is increased. Therefore, tobacco liquid dropped from the atomizing device 112 will not leak easily from the air inlet 141 via the air passage 160.

It is to noteworthy that, in other embodiments, the heating element 1122 may be oriented along a direction substantially perpendicular to an axial direction of the air pipe 113, as disclosed in CN patent application 201520048005.1.

Figure 7:
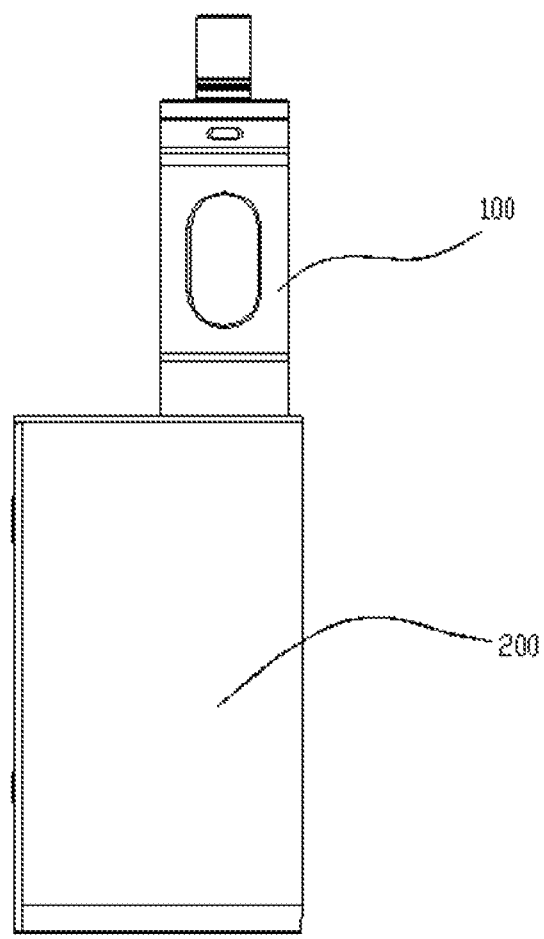
FIG. 7 is a side view of an electronic cigarette according to a second embodiment.

Referring to FIG. 7, an electronic cigarette is shown. The electronic cigarette includes an atomizer 100, and a power supply 200 detachably connected to the atomizer, e.g., via screw threads. The power supply 200 is configured for supplying the atomizer 100 power.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer for an electronic cigarette, comprising:
 a housing having a first end and an opposite second end, the second end being configured for connecting with a power supply, the housing defining a liquid chamber configured for containing tobacco liquid;
 a sealing cover detachably connected with the first end;
 a mouthpiece connected with the sealing cover;
 an atomizing device arranged in the housing, the atomizing device being configured for atomizing the tobacco liquid to form aerosol; and
 an air pipe in the housing;
 wherein the first end defines a liquid filling opening in communication with the liquid chamber, when the sealing cover is connected with the first end, the sealing cover seals the liquid filling opening;
 the sealing cover defines an air inlet, the air pipe and the liquid chamber cooperatively define an annular air passage in communication with the air inlet, so that external air can enter the air inlet and reach the atomizing device through the air passage, and then together with the aerosol can be expelled via the mouthpiece;
 the liquid chamber comprises a storing chamber and a buffer chamber, the air pipe is arranged in the storing chamber, the atomizing device is configured to absorb the tobacco liquid in the buffer chamber for atomization, the atomizer further comprises a liquid passage and a valve, the liquid passage is defined between the storing chamber and the buffer chamber, and the valve is configured for opening or closing the liquid passage.

2. The atomizer according to claim 1, wherein the valve comprises a sealing element, a movable element, and a spring, the sealing element is configured for sealing the liquid passage, the sealing element is arranged on the movable element, the spring abuts against the movable element, the movable element is nested in the air passage, and extends to the first end; when the sealing cover is connected with the first end, the sealing cover abuts against the movable element, the movable element drives the sealing element to move along an axial direction of the housing and compresses the spring, the liquid passage is opened; when the sealing cover is detached from the first end, the movable element drives the sealing element to seal the liquid passage upon a restoring force of the spring.

3. An electronic cigarette, comprising:
 an atomizer according to claim 1; and a power supply configured for supplying the atomizer power.

4. The atomizer according to claim 1, wherein the atomizing device comprises a liquid conducting element and a heating element in contact with the liquid conducting element, the liquid conducting element is configured for absorbing the tobacco liquid in the liquid chamber for atomization of the heating element.

5. The atomizer according to claim 4, wherein the liquid conducting element is made of cotton, glass fiber, or ceramic.

6. The atomizer according to claim 4, wherein the heating element is oriented parallel to an axial direction of the air pipe.

7. The atomizer according to claim 1, further comprising an air adjusting ring nesting the sealing cover, wherein the air adjusting ring defines a through hole, and is rotatable relative to the sealing cover, such that an overlapping area between the through hole and the air inlet can be changed.

8. The atomizer according to claim 7, further comprising an abutting device abutting against the air adjusting ring, wherein the abutting device is configured for providing a force on the air adjusting ring along a radial direction thereof the air adjusting ring, thus preventing the air adjusting ring from rotating relative to the sealing cover casually.

* * * * *